United States Patent [19]

Reuschling et al.

[11] Patent Number: 4,806,639
[45] Date of Patent: Feb. 21, 1989

[54] PROCESS FOR THE PREPARATION OF 6-METHYL-3,4-DIHYDRO-1,2,3-OXATHIAZIN-4-ONE 2,2-DIOXIDE AND FOR THE PURIFICATION THEREOF

[75] Inventors: Dieter Reuschling, Butzbach; Adolf Linkies, Frankfurt am Main; Walter Reimann, Hofheim am Taunus; Otto E. Schweikert, Kelkheim; Karl E. Mack, Weisbaden, all of Fed. Rep. of Germany

[73] Assignee: Hoechst Aktiengesellschaft, Frankfurt am Main, Fed. Rep. of Germany

[21] Appl. No.: 902,206

[22] Filed: Aug. 29, 1986

[30] Foreign Application Priority Data

Sep. 3, 1985 [DE] Fed. Rep. of Germany ....... 3531359

[51] Int. Cl.$^4$ .......................................... C07D 291/06
[52] U.S. Cl. .......................................................... 544/2
[58] Field of Search ............................................. 544/2

[56] References Cited

FOREIGN PATENT DOCUMENTS 2453063 5/1976 Fed. Rep. of Germany .......... 544/2

OTHER PUBLICATIONS

Fieser et al., Textbook "Organic Experiments", Heath and Co., Lex., MA, 1979, pp. 31, 32 and 34–38.
Clauss et al., Angewandte Chemie, Intl. Ed., 12, 869–876 (1973) ("Oxathiazinone Dioxides . . . ").
Petersen, Ber., 83, 551–558 (1950) ("Concerning New Reactions of Sulfamides").

*Primary Examiner*—John M. Ford

[57] ABSTRACT

6-Methyl-3,4-dihydro-1,2,3-oxathiazin-4-one 2,2-dioxide is prepared by cylcizing acetoacetamide-N-sulfonic acid or its salts with an at least approximately equimolar amount of $SO_3$ in the presence of a water-immiscible, inert organic solvent and, if appropriate, also an inert, inorganic solvent. In the event that an equimolar amount of $SO_3$ is employed, working up is effected by adding aqueous sulfuric acid when the cyclization reaction is complete; in the event that the amount of $SO_3$ employed is more than equimolar, the 6-methyl-3,4-dihydro-1,2,3-oxathiazin-4-one 2,2-dioxide obtained in the form of the $SO_3$-adduct is hydrolyzed by adding water or ice, whereby sulfuric acid is formed from the $SO_3$ combined in the $SO_3$-adduct.

The inert, organic solvent is then removed from the resulting multi-phase mixture by distillation, and the 6-methyl-3,4-dihydro-1,2,3-oxathiazin-4-one 2,2-dioxide is obtained in a pure form from the remaining aqueous sulfuric acid phase by crystallization. Additionally, quite generally, crude 6-methyl-3,4-dihydro-1,2,3-oxathiazin-4-one 2,2-dioxide is purified by recrystallization from aqueous sulfuric acid. The non-toxic salts of 6-methyl-3,4-dihydro-1,2,3-oxathiazin-4-one 2,2 dioxide—in particular the potassium salt—are valuable synthetic sweetening agents.

9 Claims, No Drawings

PROCESS FOR THE PREPARATION OF 6-METHYL-3,4-DIHYDRO-1,2,3-OXATHIAZIN-4-ONE 2,2-DIOXIDE AND FOR THE PURIFICATION THEREOF

6-Methyl-3,4-dihydro-1,2,3-oxathiazin-4-one 2,2-dioxide is the compound of the formula

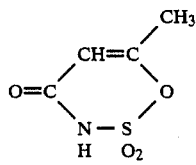

As a result of the acid hydrogen on the nitrogen atom, the compound is capable of forming salts (with bases). The non-toxic salts—such as, for example, the Na, K and Ca salt—can be used as sweetening agents in the food industry because of their sweet taste, in some cases intense sweet taste, the K salt ("Acesulfam K" or just "Acesulfam") being of particular importance.

A number of different processes are known for the preparation of 6-methyl-3,4-dihydro-1,2,3-oxathiazin-4-one 2,2-dioxide and its non-toxic salts; cf. Angewandte Chemie 85, issue 22 (1973), pages 965 to 973, corresponding to International Edition Volume 12, No. 11 (1973), pages 869-876. Virtually all the processes start from chlorosulfonyl or fluorosulfonyl isocyanate ($XSO_2NCO$ in which $X=Cl$ or $F$). The chlorosulfonyl or fluorosulfonyl isocyanate is then reacted with monomethylacetylene, acetone, acetoacetic acid, tert.-butyl acetoacetate or benzyl propenyl ether (in a multi-stage reaction in most cases) to give acetoacetamide-N-sulfochloride or acetoacetamide-N-sulfofluoride, which cyclizes under the influence of bases (such as, forexample, methanolic KOH) and affords the corresponding salts of 6-methyl-3,4-dihydro-1,2,3-oxathiazin-4-one 2,2-dioxide. The free oxathiazinone can, if desired, be obtained from the salts in a customary manner (by means of acids).

A further process for the preparation of the oxathiazin-one intermediate stage acetoacetamide N-sulfofluoride starts from sulfamoyl fluoride $H_2NSO_2F$, the partial hydrolysis product of fluorosulfonyl isocyanate (German OffenLegungsschrift No. 2,453,063). The fluoride of sulfamic acid $H_2NSO_2F$ is then reacted with an approximately equimolar amount of the acetoacetylating agent diketene in an inert organic solvent in the presence of an amine at temperatures between about $-30°$ and $100°$ C.; the reaction proceeds in accordance with the following equation (using triethylamine as the amine):

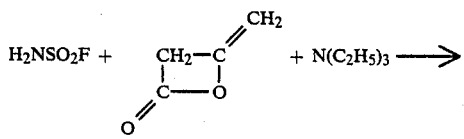

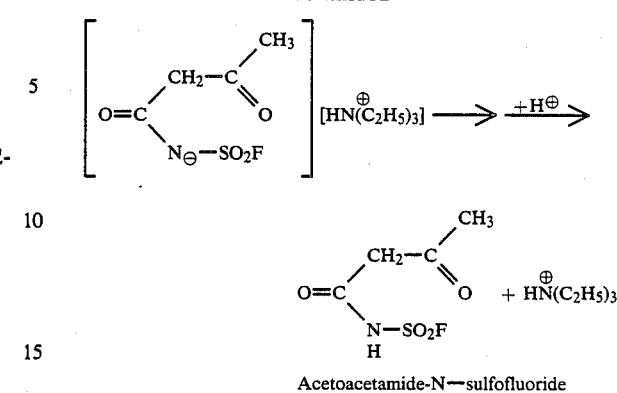

Acetoacetamide-N—sulfofluoride

The acetoacetamide-N-sulfofluoride is then cyclized to give the sweetening agent in a customary manner by means of a base, for example methanolic KOH:

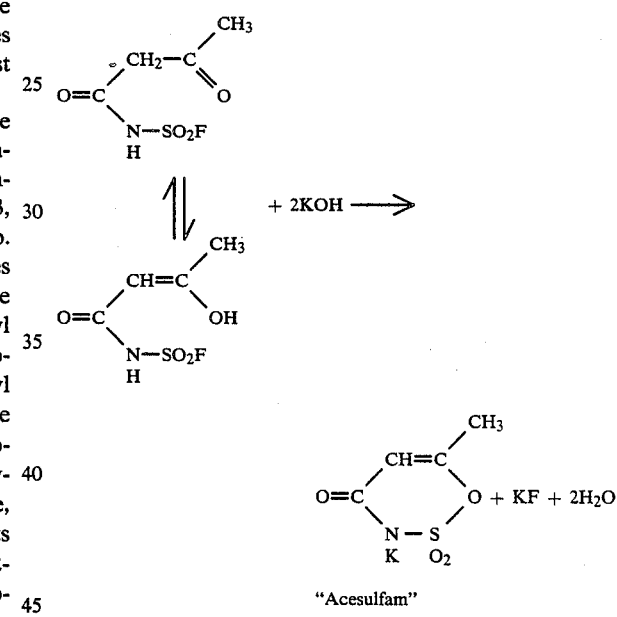

"Acesulfam"

Although the known processes give yields of 6-methyl-3,4-dihydro-1,2,3-oxathiazin-4-one 2,2-dioxide and its non-toxic salts which are in some cases quite satisfactory (up to approx. 85% of theory, relative to the sulfamoyl halide starting materials), they are still in need of improvement, particularly for industrial purposes, because of the need to employ the starting materials chlorosulfonyl fluorosulfonyl isoxyanate which are not very easily accessible; this is because, owing to the starting materials (HCN, $Cl_2$, $SO_3$ and HF), some of which are rather unpleasant to handle, the preparation of chlorosulfonyl and fluorosulfonyl isocyanate requires considerable precautionary measures and safety precautions. The preparation of chlorosulfonyl and fluorosulfonyl isocyanate is based on the following equations:

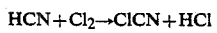

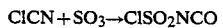

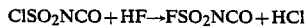

The replacement of sulfamoyl fluoride in the process according to German Offenlegungsschrift No. 2,453,063 mentioned above, for instance by sulfamic acid $H_2NSO_3H$ or salts thereof, which is considerably easier to obtain (for example from $NH_3+SO_3$), hardly seemed promising for the simple reason that the reaction of Na sulfamate $H_2NSO_3Na$ with diketene in an aqueous alkaline solution does not give any reaction product which can be isolated in a pure state. On the contrary, it has only been possible to isolate the 1:1- adduct which is formed in this reaction, probably at least together with other products in the form of the coupling product with 4-nitrophenyuldiazonium chloride as a pale yellow dyestuff; cf. Ber. 83(1950), pages 551–558, in particular page 555, last paragraph before the description of the experiments and page 558, last paragraph:

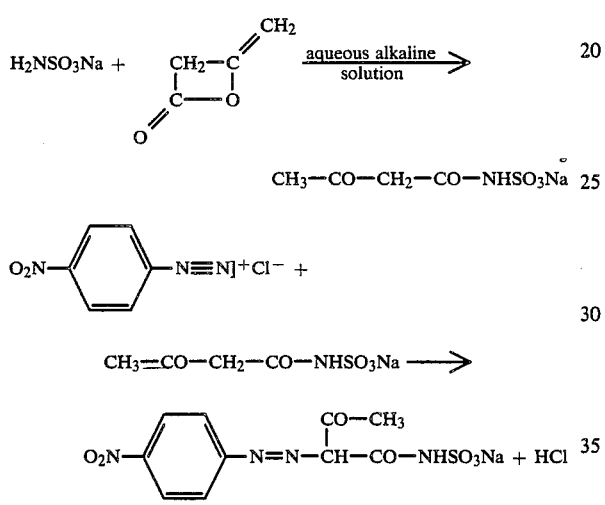

Moreover, acetoacetamide-N-sulfonic acid has otherwise been postulated only, or also, as an intermediate product in the decomposition of 6-methyl-3,4-dihydro-1,2,3-oxathiazin-4-one 2,2-dioxide when the latter is boiled in aqueous solution; cf. the literature quoted initially, Angew. Chemie (1973) (loc. cit.):

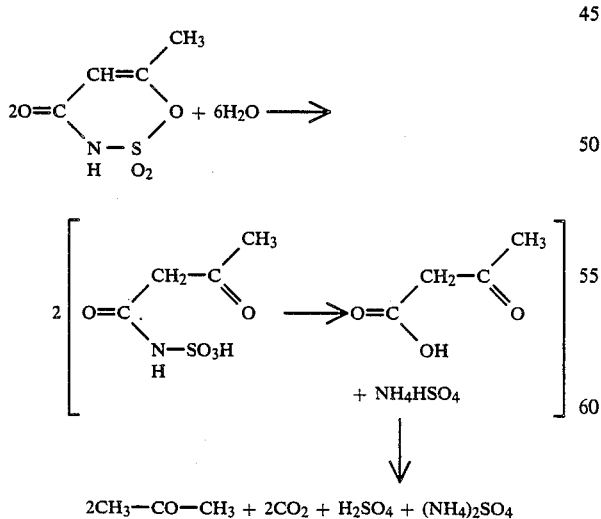

Because the processes of the state of the art for the preparation of 6-methyl-3,4-dihydro-1,2,3-oxathiazin-4-one 2,2-dioxide and its non-toxic salts are not entirely satisfactory, above all for being carried out on an industrial scale, in particular as a result of the need to employ starting materials which are not readily accessible, it was, therefore, required to improve the known processes appropriately or to develop a new, improved process.

In order to achieve this object, it has already been suggested that the process according to German Offenlegungsschrift No. 2,453,063 should be modified chiefly by replacing the sulfamoyl fluoride in the known process by salts of sulfamic acid and by subsequently cyclizing the resulting acetoacetylation product by means of $SO_3$ (European Patent Application No. 85,102,885.2—Publication Number 0,155,634—with the priority of German Application No. P 3,410,439.9 dated 22.3.1984—U.S. Pat. No. 4,607,100 (Clause et al.), issued Aug. 19, 1986.

The patent application last mentioned relates particularly to a process for the preparation of 6-methyl-3,4-dihydro-1,2,3-oxathiazin-4-one 2,2-dioxide and its non-toxic salts by (a) reacting a sulfamic acid derivative with an at least approximately equimolar amount of an acetoacetylating agent in an inert organic solvent, if appropriate in the presence of an amine or phosphine catalyst, to give an acetoacetamide derivative and (b) cyclizing the acetoacetamide derivative; the process comprises using, as the sulfamic acid derivative in stage (a), a salt of sulfamic acid which is at least partly soluble in the inert organic solvent employed, cyclizing the acetoacetamide-N-sulfonate formed in this stage or the free acetoacetamide-N-sulfonic acid in stage (b) by the action of an at least approximately equimolar amount of $SO_3$, if appropriate in an inert inorganic or organic solvent, to give 6-methyl-3,4-dihydro-1,2,3-oxathiazin-4-one 2,2-dioxide, and then, if desired, also neutralizing with a base, in a stage (c), the product obtained here in the acid form.

The following are indicated in the abovementioned patent application (using diketene as the acetoacetylating agent) as the reactions on which the process is based:

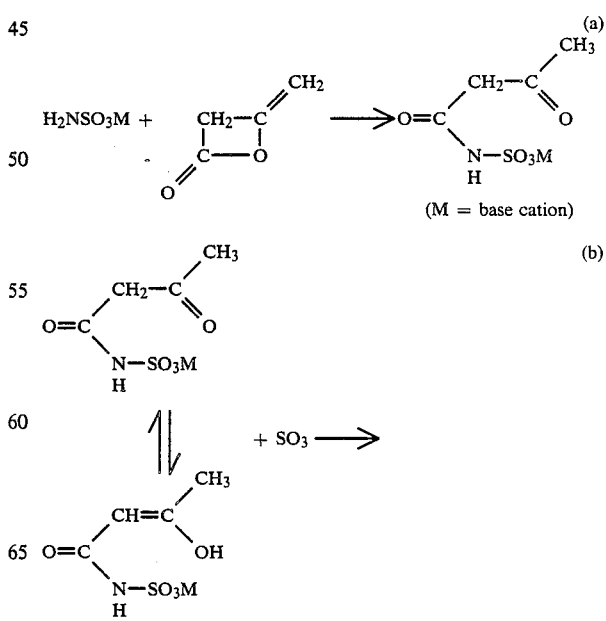

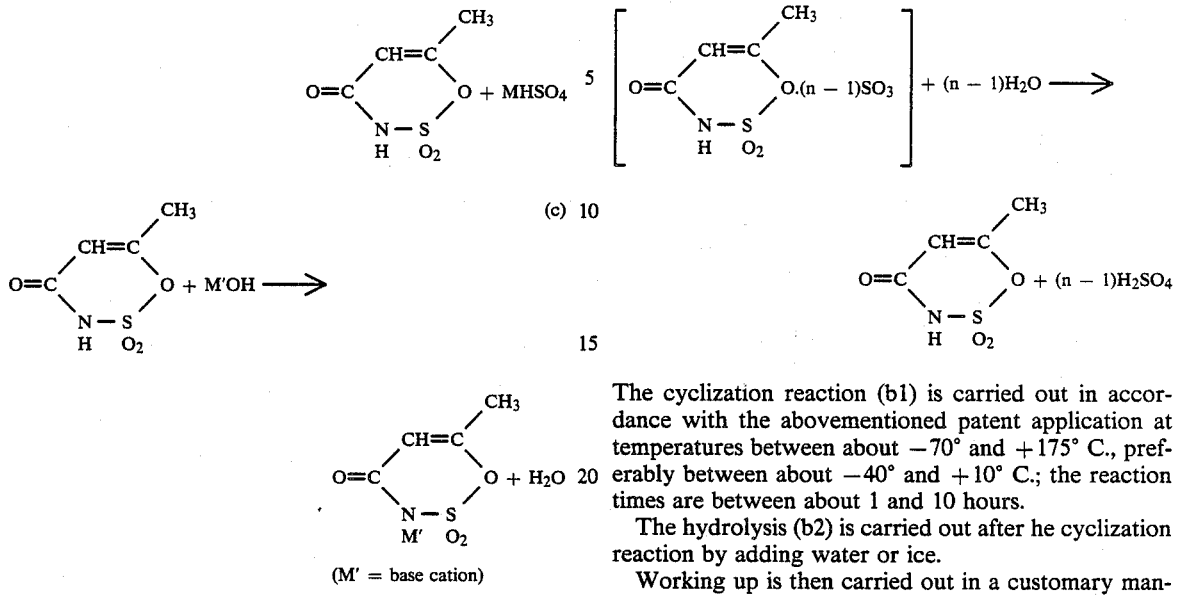

(M' = base cation)

Stage (b) in this scheme of reactions is shown with an amount of SO₃ which is equimolar in respect of the acetoacetamide-N-sulfonate. It is preferable, however, to use an excess of SO₃. An intermediate product is then formed, the chemical structure of which is not yet accurately known, but which possibly constitutes an SO₃ adduct of 6-methyl-3,4-dihydro-1,2,3-oxathiazin-4-one 2,2-dioxide—described below as the "SO₃-adduct"— —and this adduct must then also be hydrolyzed. In this case the abovementioned reaction stage (b) thus comprises 2 partial stages, namely:

b1: cyclization

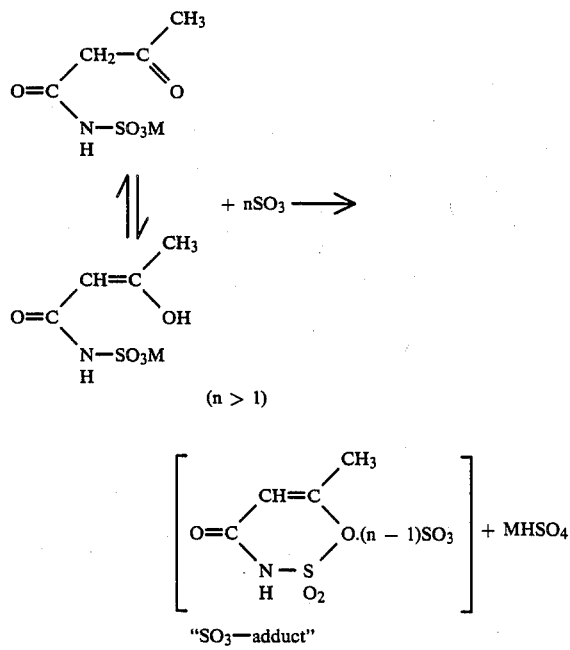

b2: Hydrolysis

The cyclization reaction (b1) is carried out in accordance with the abovementioned patent application at temperatures between about −70° and +175° C., preferably between about −40° and +10° C.; the reaction times are between about 1 and 10 hours.

The hydrolysis (b2) is carried out after the cyclization reaction by adding water or ice.

Working up is then carried out in a customary manner; working up is, however, only illustrated in detail for the preferred case in which methylene chloride is used as a reaction medium. 2 phases are formed after the hydrolysis in this case, the 6-methyl-3,4-dihydro-1,2,3-oxathiazin-4-one 2,2-dioxide passing mainly into the organic phase. The fractions still present in the aqueous sulfuric acid can be obtained by extraction with a (water-immiscible) organic solvent, such as, for example, methylene chloride or an organic ester.

Alternatively, after water has been added, the reaction solvent is removed by distillation and the 6-methyl-3,4-dihydro-1,2,3-oxathiazin-4-one 2,2-dioxide remaining in the sulfuric acid of the reaction is extracted with a more suitable organic solvent.

The combined organic phases are dried, for example with Na₂SO₄, and are concentrated. Sulfuric acid which may have been carried over in the extraction can be removed by the controlled addition of an aqueous alkali solution to the organic phase. If it is intended to isolate the 6-methyl-3,4-dihydro-1,2,3-oxathiazin-4-one 2,2-dioxide, it is advisable also to purify it in a customary manner (preferably by recrystallization). The yield is between about 70 and 95% of theory, relative to the acetoacetamide-N-sulfonate (or the free acid).

If, however, it is intended to isolate a non-toxic salt of 6-methyl-3,4-dihydro-1,2,3-oxathiazin-4-one 2,2-dioxide, the neutralization stage (c) is also carried out. This is effected by neutralizing, in a customary manner, by means of an appropriate base the oxathiazinone compound obtained in the acid form in stage (b). This is carried out, for example, by neutralizing, by means of an appropriate base—preferably a potassium base, such as, for example, KOH, KHCO₃, K₂CO₃, K alcoholates etc.—the combined, dried and concentrated organic phases at the end of stage (b) in suitable organic solvents, such as, for example, alcohols, ketones, esters or ethers or even water. Or the oxathiazinone compound is neutralized by direct extraction with an aqueous potassium base from the purified organic extraction phase (stage b). The oxathiazinone salt is then precipitated, if necessary after concentrating the solution, in a crystalline form, and can also be purified by recrystallization. The neutralization stage takes place in a virtually 100% yield.

Reference should be made to the detailed description in the patent application mentioned in regard to the further details of the process.

The process starts from readily accessible and cheap starting materials and is extremely simple to carry out. The yields of the whole process are between about 65 and 95% of theory, relative to the sulfamate starting material.

In the course of further work on this process it has also been suggested that both the cyclization reaction (b1) and the hydrolysis (b2) should be carried out within short to very short times (approx. 10 minutes down to the region of seconds and fractions of a second) (Patent Application No. P 3,527,070.5 dated 29.7.1985 - HOE 85/F 134). The practical realization of the process is preferably effected in devices which are suitable and known for carrying out reactions of this type which proceed rapidly and with the evolution of heat (thin film reactors, falling film reactors, spray reactors, tubular reactors with and without internal fitments, etc.). The reaction mixture is worked up as described in the patent application mentioned above. This "short time variant" enables the technical procedure and, in particular, the space-time yield of the process to be considerably improved.

Finally, it has also already been suggested that, instead of stages (a) and (b) of the process of the abovementioned European Patent Application No. 85,102,885.2, acetoacetamide should be reacted with an at least about twice-molar amount of SO₃, if appropriate in an inert inorganic or organic solvent (German Patent Application No. P 3,410,440.2 dated 22.3.1984 - HOE 84/F 065). In this case acetoacetamide-N-sulfonic acid is probably first formed in one stage from one mole of acetoacetamide and one mole of SO₃, and then undergoes cyclization with a further mole of SO₃ to give 6-methyl-3,4-dihydro-1,2,3- oxathiazin-4-one 2,2-dioxide in accordance with the following scheme of reactions:

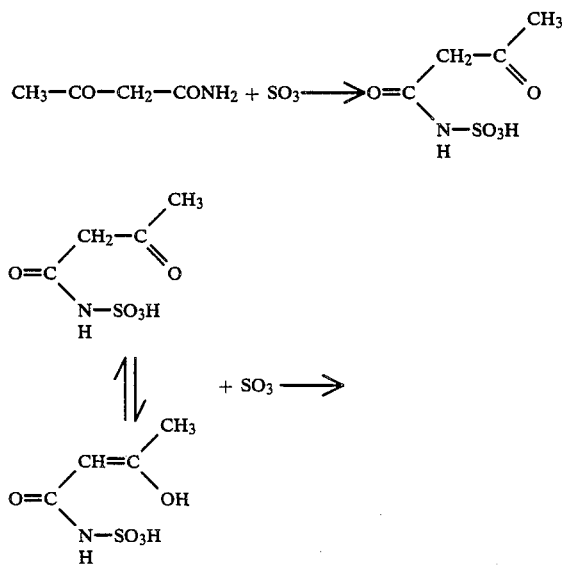

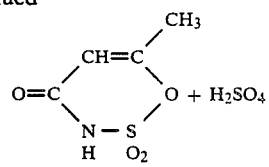

Here too the "SO₃ adduct" is formed with excess SO₃ and must also be hydrolyzed in order to liberate the 6-methyl-3,4-dihydro-1,2,3-oxathiazin-4-one 2,2-dioxide. The working up of the hydrolyzed mixture and, if desired, the conversion of the 6-methyl-3,4-dihydro-1,2,3-oxathiazin-4-one 2,2-dioxide into its non-toxic salts are effected, in principle, in the same way as that described in the above-mentioned European Patent Application No. 85,102,885.2. The yield figures for 6-methyl-3,4-dihydro-1,2,3-oxathiazin-4-one 2,2-dioxide are between about 30 and 90% of theory, relative to the acetoacetamide starting material.

In all three of the abovementioned patent applications the 6-methyl-3,4-dihydro-1,2,3-oxathiazin-4-one 2,2-dioxide which has been liberated in the hydrolysis of the "SO₃-adduct" is obtained from the organic phase which is formed, after adding water, when using a (water-immiscible) organic solvent for the reaction and/or which is formed if the reaction sulfuric acid is extracted with organic solvents. However, the 6-methyl-3,4-dihydro-1,2,3-oxathiazin-4-one 2,2-dioxide thus obtained and also the non-toxic salts optionally obtained therefrom by reaction with appropriate bases are not always of the required purity, so that various purification operations—preferably recrystallization(s) are often also necessary—involving additional outlay and also associated with loss of substance.

In developing the abovementioned processes further, it has now been found that a considerably purer 6-methyl-3,4-dihydro-1,2,3-oxathiazin-4-one 2,2-dioxide is obtained if it is isolated, not—as described above—from the organic phase, but from the aqueous sulfuric acid phase in a direct manner by crystallization.

The invention relates to a process for the preparation of 6-methyl-3,4-dihydro-1,2,3-oxathiazin-4-one 2,2-dioxide by cyclizing an acetoacetamide derivative; the process comprises using acetoacetamide-N-sulfonic acid or its salts—dissolved in a water-immiscible, inert organic solvent—as the acetoacetamide derivative, carrying out the cyclization by treatment with an at least approximately equimolar amount of SO₃—if appropriate dissolved similarly in a water-immiscible, inert, organic solvent or in an inert, inorganic solvent—adding aqueous sulfuric acid when the cyclization reaction is complete if an equimolar amount of SO₃ has been employed or—in the event that a more than equimolar amount of SO₃ has been employed, hydrolyzing the 6-methyl-3,4-dihydro-1,2,3- oxathiazin-4-one 2,2-dioxide obtained as the SO₃-adduct after the cyclization reaction, and removing the inert organic solvent from the resulting multi-phase mixture by distillation, and isolating the 6-methyl-3,4-dihydro-1,2,3-oxathiazin-4-one 2,2-dioxide from the residual aqueous sulfuric acid phase by crystallization.

The smooth success of the cyclization of acetoacetamide-N-sulfonic acid and its salts with SO₃ is very surprising, because the elimination of water or bases which takes place with cyclization is not successful, or is in any case not successful for practical purposes, as is known, with other agents for eliminating water or bases, such as, for example, $P_2O_5$, acetic anhydride, trifluoroacetic anhydride, thionyl chloride etc., as it has already been possible to show in the abovementioned European Patent Application No. 85,102,885.2 by means of a comparison example (using $P_2O_5$).

Additionally, it is surprising that, when the 6-methyl-3,4-dihydro-1,2,3-oxathiazin-4-one 2,2-dioxide crystallizes from sulfuric acid, a product is obtained which, apart from small amounts of adhering sulfuric acid (which can, however, easily be removed), contains virtually no impurities—at all events virtually no impurities of an organic nature—since it would have been entirely possible to expect that possible dissolved organic impurities—originating from the previous reaction—would crystallize out together with the 6-methyl-3,4-dihydro-1,2,3-oxathiazin-4-one 2,2-dioxide.

The preparation of the acetoacetamide-N-sulfonic acid starting material and its salts is preferably effected by stage (a) of the process of the abovementioned European Patent Application No. 85,102,885.2 by reacting the Li or ammonium salts of sulfamic acid with diketene in inert organic solvents. Solutions of the Li and ammonium salts of acetoacetamide-N-sulfonic acid which can be employed as such without further treatment for the cyclization reaction with $SO_3$ are obtained in this process.

It is, of course, also possible to use other salts of acetoacetamide-N-sulfonic acid—in particular alkali and alkaline earth metal salts—for the cyclization reaction mentioned. Compared with using the salts, the use of free acetoacetamide-N-sulfonic acid hardly affords any advantages.

As in the case of the salts, it is also possible to employ the free acetoacetamide-N-sulfonic acid for the cyclization reaction directly, in the corresponding solution such as is obtained in its preparation. The solution of the free acetoacetamide-N-sulfonic acid which is probably formed as an intermediate in the process of German Patent Application No. P 3,410,440.2 (HOE 84/F 065) can also be regarded as a solution such as is obtained in its preparation.

Inert organic solvents which are suitable for acetoacetamide-N-sulfonic acid or its salts are appropriately those solvents from the series of inert organic solvents listed in the abovementioned patent applications which are immiscible with water and which boil below 100° C. (under normal pressure), i.e.: halogenated aliphatic hydrocarbons, preferably those having up to 4 carbon atoms, such as, for example, methylene chloride, chloroform, 1,2-dichloroethane, trichloroethylene, trichlorofluoroethylene etc., and also carbonic acid esters of lower aliphatic alcohols,ppreferably methanol.

The organic solvents can be employed either on their own or as a mixture.

Halogenated aliphatic hydrocarbons, especially methylene chloride, are particularly preferred solvents.

The concentration of acetoacetamide-N-sulfonic acid or its salts in the inert solvent is not critical, but is limited on the one hand by the solubility and on the other hand by considerations of economy, since, at high dilution, a great deal of solvent has to be subsequently removed and worked up again. In general, concentrations between about 0.1 and 2 mole of acetoacetamide-N-sulfonic acid or its salts per liter are appropriate.

The $SO_3$ can be added either in a solid or liquid form or by condensing in $SO_3$ vapor. It is preferable, however, to add it in dissolved form, in particular dissolved in a water-immiscible, inert organic solvent or in an inert inorganic solvent.

The suitable water-imiscible, inert organic solvents are, in principle, the same as those which are also used for dissolving the acetoacetamide-N-sulfonic acid or its salts.

Examples of inert inorganic solvents which can be employed are concentrated sulfuric acid or liquid $SO_2$. The amount of inert solvent employed for the $SO_3$ is, in principle, not critical either. If a solvent is employed, it is merely necessary to insure that the $SO_3$ is adequately dissolved; an upper limit is set to the amount of solvent by considerations of economy. Advantageous concentrations are about 5 to 50% by weight, preferably about 15 to 30% by weight, of $SO_3$.

In a preferred embodiment of the invention the same inert solvent, preferably a solvent from the group of halogenated aliphatic hydrocarbons, in particular only methylene chloride, is used both for the acetoacetamide-N-sulfonic acid or its salts and for the $SO_3$.

Although the molar ratio of acetoacetamide-N-sulfonic acid or acetoacetamide-N-sulfonate to $SO_3$ can be about 1:1, an excess of $SO_3$ of up to about 20-fold, preferably a 3-fold to 10-fold and especially about 4-fold to 7-fold molar excess, is preferable.

In other respects, the cyclization reaction is carried out, in principle, in the same manner and under the same conditions as is described in the 3 patent applications mentioned above.

As can be seen from the reaction schemes illustrated at the outset, no "$SO_3$-adduct" is formed if the acetoacetamide-N-sulfonic acid or its salts and the $SO_3$ are employed in an equimolar ratio. Hydrolysis is therefore not necessary in this case. Sulfuric acid, preferably of a concentration between about 20 and 90%, in particular between about 50 and 85%, is added in this case for the isolation of pure 6-methyl-3,4-dihydro-1,2,3-oxathiazin-4-one 2,2-dioxide. The amount of sulfuric acid should be such that good crystallization is possible, without too much product remaining in solution; the amount which is advantageous in a particular case can be determined easily by a few simple small-scale tests.

In the preferred case of using acetoacetamide-N-sulfonic acid or its salts and $SO_3$ in a molar ratio of 1: more than 1, an "$SO_3$-adduct" is formed in the cyclization reaction, and it is necessary to liberate the 6-methyl-3,4-dihydro-1,2,3-oxathiazin-4-one 2,2-dioxide from this by hydrolysis. Hydrolysis is effected by adding water or ice, appropriately in a molar ratio of about 2-fold to 6-fold—in relation to the excess of $SO_3$ used.

A 2-phase or (if 6-methyl-3,4-dihydro-1,2,3-oxathiazin4-one 2,2-dioxide has already been precipitated) a 3-phase mixture is present after sulfuric acid has been added after the cyclization reaction using acetoacetamide-N-sulfonic acid or acetoacetamide-N-sulfonate and $SO_3$ in a 1:1 molar ratio and also after the hydrolysis subsequent to the cyclization reaction using acetoacetamide-N-sulfonic acid or acetoacetamide-N-sulfonate in a molar ratio of 1: more than 1. The bulk of the 6-methyl-3,4-dihydro-1,2,3-oxathiazin-4-one 2,2-dioxide present is dissolved in the organic phase and in the sulfuric acid phase. If the inert organic solvent has already been removed, for example by evaporation in accordance with the "short-time variant" of Patent Application No. P 3,527,070.5, HOE 85/F 134), the 6-methyl-3,4-dihydro-1,2,3-oxathiazin-4-one 2,2-dioxide present is mainly dissolved only in the sulfuric acid phase.

If, however, an organic phase is still present, the inert organic solvent is removed from the whole multi-phase mixture by distillation. The distillation can be carried out in vacuo, under atmospheric pressure or under an excess pressure. If, for example, methylene chloride, which is the particularly preferred solvent, is used, distillation is advantageously carried out under pressures of about 200 mbar to 1 bar and at temperatures of about 0° to 42° C.

The distillation can be carried out either discontinuously or continuously. In the discontinuous procedure, the solvent can be distilled off directly from the reaction vessel. Continuous distillation with short dwell times is preferred, however, since this is the best way of avoiding possible thermal decomposition of the 6-methyl-3,4-dihydro-1,2,3-oxathiazin-4-one 2,2-dioxide. The inert organic solvent used for the cyclization reaction is obtained as the distillate in an unpolluted form.

The sulfuric acid phase remaining after the distillation contains all the 6-methyl-3,4-dihydro-1,2,3-oxathiazin-4-one 2,2-dioxide, but also all the byproducts and impurities. If the removal of the organic solvent by distillation has been carried out at elevated temperatures, the sulfuric acid phase is also at an elevated temperature. On cooling, the 6-methyl-3,4-dihydro-1,2,3-oxathiazin-4-one 2,2-dioxide crystallizes out in a surprisingly high degree of purity—in particular free from organic impurities.

If the organic solvent has been removed by distillation at a fairly low temperature, it is no longer possible, in some cases, to cool the sulfuric acid phase overmuch until solidification takes place. In this case it can be expedient to concentrate the sulfuric acid phase, as far as possible under reduced pressure, as a result of which crystals of 6-methyl-3,4-dihydro-1,2,3-oxathiazin-4-one 2,2-dioxide are then precipitated.

If a precipitate has already been formed at the end of the cyclization reaction and/or when the organic solvent is removed by distillation, it can also be expedient to cause this precipitate to dissolve by warming the sulfuric acid phase or, if appropriate, also by adding further sulfuric acid, and then to induce crystallization by means of cooling.

The crystals are filtered off, and the filter cake is appropriately washed with fresh sulfuric acid, preferably sulfuric acid of about 20 to 30% strength, in order to displace the sulfuric acid mother liquor, and is thoroughly suction-drained. The filter cake obtained has a slight residual moisture of aqueous sulfuric acid, but is free, or at all events virtually free, from organic byproducts. If a product free from residual sulfuric acid is also desired, it is still possible to recrystallize the crystals.

If, however, the intention is not to isolate pure 6-methyl-3,4-dihydro-1,2,3-oxathiazin-4-one 2,2-dioxide, but to obtain non-toxic salts thereof—in particular the potassium salt—the crystals of 6-methyl-3,4-dihydro-1,2,3-oxathiazin-4-one 2,2-dioxide which still contain a slight residual moisture of aqueous sulfuric acid can be converted directly into the corresponding salts by neutralization. In principle, the neutralization is carried out in the same manner as that described in European Patent Application No. 85,102,885.2. This is effected by dissolving the product to be neutralized in water or in organic solvents, such as, for example, alcohols, ketones, esters or ethers—preferably only in water—and neutralizing it with an appropriate base, in particular a potassium base, such as, for example, KOH, KHCO$_3$, K$_2$CO$_3$ or a K alcoholate.

In a preferred embodiment of the neutralization, the 6-methyl-3,4-dihydro-1,2,3-oxathiazin-4-one 2,2-dioxide is dissolved in an approximately equal amount of water at temperatures between about 0° and 100° C., preferably between about 20° and 80° C., and is neutralized with potassium hydroxide solution of approximately 45 to 50% strength. After the neutralization, the aqueous suspension of the potassium salt is cooled and filtered. Owing to the relatively good solubility of the potassium salt in water, cooling to 0° to about 10° C. is advisable. Since the non-recrystallized 6-methyl-3,4-dihydro-1,2,3-oxathiazin-4-one 2,2-dioxide still contains a slight residual moisture of sulfuric acid, a small amount of potassium sulfate is also formed together with the desired potassium salt in the neutralization with a potassium base. However, because of the good solubility of potassium sulfate in water, virtually all of the potassium sulfate remains in the neutralization mother liquor.

After drying, the potassium salt of 6-methyl-3,4-dihydro-1,2,3-oxathiazin-4-one 2,2-dioxide (Acesulfam K) has a purity of over 99.5%. The small residue is composed almost exclusively of potassium sulfate.

The extent of isolation of Acesulfam K in this embodiment of neutralization is about 80–90% of theory, relative to the 6-methyl-3,4-dihydro-1,2,3-oxathiazin-4-one 2,2-dioxide employed. The proportion of Acesulfam K remaining in the neutralization mother liquor corresponds to its solubility in water. The extent of isolation can be increased if less water is used to dissolve the 6-methyl-3,4-dihydro-1,2,3-oxathiazin-4-one 2,2-dioxide; the resulting suspension of Acesulfam K then becomes thicker, however.

If an even lower content of potassium sulfate in the Acesulfam K is desired, a recrystallization from water can also be carried out subsequently. By this means the Acesulfam K is obtained in virtually 100% purity. The mother liquor from the recrystallization can ee recycled for dissolving the 6-methyl-3,4-dihydro-1,2,3-oxathiazin-4-one 2,2-dioxide, so that no loss in yield occurs.

A further optimization of the yield can, if appropriate, also be carried out by extracting the product remaining dissolved in the sulfuric acid mother liquor after the 6-methyl-3,4-dihydro-1,2,3-oxathiazin-4-one 2,2-dioxide has been filtered off from the sulfuric acid phase with a water-immiscible, inert organic solvent—if possible the same solvent which was also used for carrying out the cyclization reaction—and combining the extract with the reaction product prior to the distillation of the solvent.

Concentrating the neutralization mother liquor can also be regarded as a measure for optimizing the yield further.

The yields from the cyclization process according to the invention and the subsequent isolation of the product are of the same order of magnitude as the yields indicated in the three patent applications mentioned above; a higher purity of product is, however, obtained by means of the invention.

Finally, the isolation of the product carried out in accordance with the invention subsequent to the cyclization reaction can also be utilized to purify impure 6-methyl-3,4-dihydro-1,2,3-oxathiazin-4-one 2,2-dioxide prepared by other means.

The invention also relates, therefore, to a process for the purification of 6-methyl-3,4-dihydro-1,2,3-oxathiazin-4-one 2,2-dioxide, which comprises recrystallizing crude 6-methyl-3,4-dihydro-1,2,3-oxathiazin-4-one 2,2-dioxide from aqueous sulfuric acid—preferably sulfuric acid of about 20 to 90% strength, in particular about 50 to 85% strength.

Any inorganic or organic impurities present in the crude 6-methyl-3,4-dihydro-1,2,3-oxathiazin-4-one 2,2-dioxide are completely or at all events virtually completely, removed by means of this recrystallization.

The examples which follow are intended to illustrate the invention further. The examples of the invention (A) are followed by a comparison example (B), from which it can be seen that a less pure 6-methyl-3,4-dihydro-1,2,3-oxathiazin-4-one 2,2-dioxide is obtained if the latter is isolated, not from the sulfuric acid phase, but from the organic phase. In the examples 6-methyl-3,4-dihydro-1,2,3-oxathiazin-4-one 2,2-dioxide is abbreviated to "ASH", and its potassium salt to "ASK".

Preparation of the acetoacetamide-N-sulfonate used as the starting material for the examples 48.6 g (=0.5 mol) of sulfamic acid in 250 ml of $CH_2Cl_2$ were neutralized with 52.5 g (=0.53 mol) of triethylamine while cooling so that the temperature did not exceed +30° C. 3 g of acetic acid were added. 46.3 g (=0.55 mol) of diketene were added dropwise at 0° C. in the course of 60 minutes. The mixture was then stirred for 60 minutes at 0° C. and for 6 hours at room temperature.

(A) Examples of the invention

EXAMPLE 1

(a) Cyclization and hydrolysis:

500 ml of $CH_2Cl_2$ were initially placed in a reaction vessel and were cooled to −30° C. The solution of triethylammonium acetoacetamide-N-sulfonate prepared as above and 120 ml (=2.8 mol) of $SO_3$ were added dropwise simultaneously. The temperature in the reaction vessel did not exceed −30° C. The mixture was then stirred for a further 30 minutes at −30° C. 162 ml of water were then added dropwise at −15° C. to −10° C. and the mixture was stirred for 1.5 hours at 0° C.

The reaction product was a three-phase mixture composed of a $CH_2Cl_2$ phase, an $H_2SO_4$ phase and solid ASH.

(b) Working up:

The $CH_2Cl_2$ was distilled off from the reaction product by vacuum distillation at 500 mbar and a boiling point of 24° C. In the course of this the maximum temperature in the bottom product did not exceed 40° C. The suspension of ASH in sulfuric acid was cooled to 0° C. and filtered off by means of a glass suction filter. The filter cake was washed on the suction filter with 50 ml of 30% strength $H_2SO_4$ and was suction-drained.

The filter cake of ASH was analysed by potentiometric titration. It contained 92% of ASH and 2.5% of $H_2SO_4$. The remainder up to 100% was water. No organic byproducts could be found in HPLC (=high pressure liquid chromatography) analysis.

The yield of ASH was 49.8 g (=0.31 mol)=61% of theory, relative to the sulfamic acid originally employed.

The ASH was converted into the K salt by dissolving it in 61 ml of water at 30° C. and neutralizing the solution at 30° C. with 50% strength KOH until pH 7 was reached. The suspension of ASK formed was cooled to 0° C. and filtered. After being dried in a vacuum drying cabinet at 200 mm Hg and 60° C., 52.3 g of ASK were obtained, corresponding to a yield of 52% of theory, relative to sulfamic acid. The ASK was white. Its purity was determined by means of potentiometric titration and HPLC. ASK: 99.9%; $K_2SO_4$: 0.1%; KCl: 20 ppm. Organic byproducts could not be detected by the HPLC.

After the ASK had been recrystallized from 0.8 times its amount of water, its content of $K_2SO_4$ was below 100 ppm.

EXAMPLE 2

The $CH_2Cl_2$ was removed by distillation under normal pressure, boiling point 42° C./1 bar, from the reaction product prepared in accordance with Example 1(a). The maximum temperature of the bottom product did not exceed 70° C. toward the end of the distillation. On cooling, crystals were precipitated from the sulfuric acid phase, and were filtered off at 0° C. and washed with 50 ml of 30% strength sulfuric acid. The filter cake contained 90% of ASH and 3.5% of $H_2SO_4$.

The yield was 54 g (=0.33 mol) =66% of theory, relative to sulfamic acid.

Neutralization was carried out as described in Example 1(b). This gave an ASK containing 99.8% of ASK and 0.2% of $K_2SO_4$.

The yield was 54 g (=0.27 mol) =54% of theory, relative to sulfamic acid.

After one recrystallization the content of ASK was 100%. No byproducts were found in the HPLC analysis.

EXAMPLES 3–6

The reaction product prepared in accordance with Example 1(a) was worked up and neutralized as described in Example 2. After the ASH had been filtered off from the sulfuric acid phase and had been washed with 30% strength sulfuric acid, the sulfuric acid phase was extracted with twice 250 ml of methylene chloride. The extract was combined with the reation product from the following experiment in each case. The mother liquor obtained in the recrystallization of the ASK was employed to dissolve the ASH in the neutralization stage of the following experiment in each case. The results of Examples 3–6 can be seen in Table 1.

TABLE 1

| Example | | ASH filter cake | | ASK | | | Recrystallized ASK | | |
|---|---|---|---|---|---|---|---|---|---|
| | | Yield: % | Purity: % | Yield: % | Purity: ASK | $K_2SO_4$ | Yield: % | Purity: % ASK | $K_2SO_4$ |
| 3 | Starting experiment | 69 | 91 | 56 | 99.5 | 0.2 | 48 | 100 | 0.03 |
| 4 | Recycling of extract and mother liquor | 67 | 90 | 63 | 99.8 | 0.1 | 54 | 100 | 0.03 |
| 5 | Recycling of extract and mother liquor | 71 | 91 | 67 | 99.8 | 0.2 | 57 | 100 | 0.01 |
| 6 | Recycling of extract | 71 | 93 | 66 | 99.5 | 0.3 | 56 | 100 | 0.03 |

TABLE 1-continued

| | ASH filter cake | | ASK | | | Recrystallized ASK | | |
|---|---|---|---|---|---|---|---|---|
| | Yield: | Purity: | Yield: | Purity: | | Yield: | Purity: % | |
| Example | % | % | % | ASK | K₂SO₄ | % | ASK | K₂SO₄ |
| and mother liquor | | | | | | | | |

EXAMPLE 7

The reaction product prepared in accordance with Example 1(a). was metered from a stirred operation vessel into a thin film evaporator. The throughput rate and the heat input were adjusted so as to give an exit temperature of 60° C. The ASH crystallized out on cooling from the emerging sulfuric acid phase. Inclusive of the extraction of ASH from the sulfuric acid mother liquor and the recycling of crystallization mother liquor, an ASH yield of 71% of theory was obtained. The ASH filter cake contained 94% of ASH and 2% of $H_2SO_4$.

Neutralization was carried out in accordance with Example 1. The resulting ASK contained 99.6% of ASK and 0.3% of $K_2SO_4$.

(B) Comparison example

The methylene chloride phase in the reaction product prepared in accordance with inventive example (A)1 was separated off from the sulfuric acid phase, and the sulfuric acid phase was extracted by shaking with twice 250 ml of $CH_2Cl_2$. The combined methylene chloride phases were dried with sodium sulfate. When the $CH_2Cl_2$ had been removed by distillation, the ASH was obtained in the form of a pale yellow oily residue.

After being dissolved in 60 ml of $H_2O$, the ASH was neutralized with 50% strength KOH to give ASK, and the latter was dried in vacuo. This gave a pale yellow ASK containing 85% of ASK and 5% of potassium sulfate.

The yield was 66 g (=0.33 mol)=65% of theory, relative to sulfamic acid.

We claim:

1. A process for the preparation of 6-methyl-3,4-dihydro-1,2,3-oxathiazine-4-one 2,2-dioxide by cyclizing an aectoacetamide derivative, which comprises using acetoacetamide-N-sulfonic acid or its salts—dissolved in a water-immiscible, inert, organic solvent—as the acetoacetamide derivative, carrying out the cyclization by treatment with an excess of up to 20-fold molar amount of $SO_3$, hydrolyzing the 6-methyl-3,4-dihydro-1,2,3-oxathiazin-4-one 2,2-dioxide obtained in the form of the $SO_3$-adduct after the cyclization reaction, removing the inert, organic solvent from the resulting multiphase mixture by distillation, and isolating the 6-methyl-3,4-dihydro-1,2,3-oxathiazin-4-one 2,2-dioxide by crystallization from the remaining aqueous sulfuric acid phase.

2. The process as claimed in claim 1, wherein solutions of acetoacetamide-N-sulfonic acid or salts thereof and of $SO_3$ in the same water-immiscible, inert, organic solvent, are used.

3. The process as claimed in claim 1, wherein the cyclization is carried out by treatment with a 3-fold to 10-fold molar excess of $SO_3$, relative to the acetoacetamide-N-sulfonic acid or its salts.

4. Process as claimed in claim 1, wherein the $SO_3$ is dissolved in a water-immiscible inert organic solvent or in an inert inorganic solvent.

5. Process as claimed in claim 2, wherein the organic solvent is an aliphatic chlorinated hydrocarbon.

6. Process as claimed in claim 5, wherein the aliphatic chlorinated hydrocarbon is methylene chloride.

7. A prcess as claimed in claim I, wherein the cyclization is carried out by treatment with a 4-fold to 7-fold excess of $SO_3$, relative to the acetoacetamide-N-sulfonic acid or its salts.

8. A process as claimed in claim 1, wherein hydrolizing is effect by adding water or ice in a molar ratio of 2-fold to 6-fold in relation to the excess of $SO_3$ used.

9. A process as claimed in claim 1, wherein the 6-methyl-3,4-dihydro-1,2,3-oxathiazin-4-one 2,2-dioxide obtained after crystallization is converted to a non-toxic salt thereof by neutralization.

* * * * *